US011172868B2

(12) United States Patent
Zheng et al.

(10) Patent No.: US 11,172,868 B2
(45) Date of Patent: Nov. 16, 2021

(54) SCREENING OF MALIGNANT GLIOMA, BRAIN TUMORS, AND BRAIN INJURIES USING DISTURBANCE COEFFICIENT, DIFFERENTIAL IMPEDANCES, AND ARTIFICIAL NEURAL NETWORK

(71) Applicants: Yi Zheng, Cold Spring, MN (US); Anna Zheng, Cold Spring, MN (US); Qi Wu, ChongQing (CN); Hui Jiang, ChongQing (CN); Shun Zhang, ChongQing (CN); Weining Hu, Cold Spring, MN (US)

(72) Inventors: Yi Zheng, Cold Spring, MN (US); Anna Zheng, Cold Spring, MN (US); Qi Wu, ChongQing (CN); Hui Jiang, ChongQing (CN); Shun Zhang, ChongQing (CN); Weining Hu, Cold Spring, MN (US)

( * ) Notice: Subject to any disclaimer, the term of this patent is extended or adjusted under 35 U.S.C. 154(b) by 543 days.

(21) Appl. No.: 16/041,084

(22) Filed: Jul. 20, 2018

(65) Prior Publication Data

US 2019/0021647 A1    Jan. 24, 2019

Related U.S. Application Data

(60) Provisional application No. 62/535,445, filed on Jul. 21, 2017.

(51) Int. Cl.
*A61B 5/00* (2006.01)
*A61B 5/053* (2021.01)
*G06N 3/08* (2006.01)

(52) U.S. Cl.
CPC ............ *A61B 5/4064* (2013.01); *A61B 5/053* (2013.01); *A61B 5/6814* (2013.01);
(Continued)

(58) Field of Classification Search
CPC .............. A61N 1/36139; A61N 1/0534; A61N 1/36082; A61N 1/36067; A61N 1/0531;
(Continued)

(56) References Cited

U.S. PATENT DOCUMENTS

| | | | | |
|---|---|---|---|---|
| 6,061,593 A | * | 5/2000 | Fischell | A61B 5/6814 600/544 |
| 6,597,954 B1 | * | 7/2003 | Pless | A61B 5/0476 600/544 |

(Continued)

*Primary Examiner* — May A Abouelela
(74) *Attorney, Agent, or Firm* — Merchant & Gould P.C.

(57) ABSTRACT

A system and method to screen for malignant gliomas, other brain tumors, and brain injuries use disturbance coefficient, differential impedances, and artificial neural networks. The system uses prescribed excitation signals with several system configurations to measure the differential impedances, calculate harmonic responses and nonlinearity of brain tissue, and estimate the disturbance coefficient that indicates the likelihood of malignant gliomas, other brain tumors, and brain injuries. The disturbance coefficient is a weighted sum of many parameters such as receiving differential impedances, transmission differential impedances, harmonic responses, frequency dispersion, and nonlinear responses using different system configurations and different excitation signals. The method includes arranging the transmitters, receivers, and transmission lines to maximize the sensitivity of detecting brain tissue condition. The artificial neural network is trained to estimate the disturbance coefficient using clinical data. The method provides a sensitive and cost effective approach for screening malignant gliomas, other brain tumors, and brain injuries.

24 Claims, 21 Drawing Sheets

(52) U.S. Cl.
CPC .......... *A61B 5/7225* (2013.01); *A61B 5/7239* (2013.01); *A61B 5/7267* (2013.01); *A61B 5/7282* (2013.01); *A61B 5/725* (2013.01); *A61B 5/7257* (2013.01); *A61B 2560/0223* (2013.01); *G06N 3/08* (2013.01)

(58) Field of Classification Search
CPC ............ A61N 1/36014; A61N 1/36025; A61N 1/36064; A61N 1/0551; A61N 1/36053; A61B 5/6803; A61B 5/6814; A61B 2560/0223; A61B 5/165; A61B 5/6868; A61B 5/4064; A61B 5/053; A61B 5/7239; A61B 5/7282; A61B 5/7225; A61B 5/7267; A61B 5/7257; A61B 5/725; G06F 3/012; G06F 3/015; G16H 40/67; G16H 50/70; G06N 3/08
USPC .................... 600/301, 486, 547, 544; 607/45
See application file for complete search history.

(56) References Cited

U.S. PATENT DOCUMENTS

| | | | | |
|---|---|---|---|---|
| 7,747,325 B2* | 6/2010 | Dilorenzo | ............ | A61B 5/4082 607/45 |
| 8,594,779 B2* | 11/2013 | Denison | ............... | A61B 5/4094 600/544 |
| 8,786,624 B2* | 7/2014 | Echauz | ................. | A61B 5/076 345/589 |
| 9,307,918 B2* | 4/2016 | Kinrot | ................. | A61B 5/6803 |
| 10,149,624 B2* | 12/2018 | Kuenen | ................. | A61B 3/1241 |
| 2001/0051819 A1* | 12/2001 | Fischell | ............. | A61N 1/37235 607/45 |
| 2002/0082514 A1* | 6/2002 | Williams | ............. | A61B 5/6843 600/544 |
| 2003/0004428 A1* | 1/2003 | Pless | .................... | A61B 5/6868 600/544 |
| 2005/0021103 A1* | 1/2005 | DiLorenzo | ........... | A61N 1/3605 607/45 |
| 2005/0182338 A1* | 8/2005 | Huiku | .................. | A61B 5/4821 600/544 |
| 2006/0173510 A1* | 8/2006 | Besio | ................. | A61N 1/36025 607/45 |
| 2006/0264777 A1* | 11/2006 | Drew | ..................... | A61B 5/048 600/547 |
| 2007/0123758 A1* | 5/2007 | Miesel | .................. | A61B 5/1116 600/301 |
| 2009/0149913 A1* | 6/2009 | Putz | ..................... | A61B 5/0476 607/45 |
| 2010/0121214 A1* | 5/2010 | Giftakis | ............. | A61N 1/36082 600/544 |
| 2015/0190070 A1* | 7/2015 | Bonmassar | .......... | A61B 5/6814 600/383 |
| 2015/0359448 A1* | 12/2015 | Beach | .................... | A61B 5/024 600/301 |
| 2016/0058358 A1* | 3/2016 | Marcovitch | ........... | G16H 40/63 600/547 |
| 2017/0215753 A1* | 8/2017 | Lee | ......................... | A61B 5/24 |
| 2018/0206784 A1* | 7/2018 | Jensen | .................. | G16H 50/20 |
| 2019/0001133 A1* | 1/2019 | Onarheim | .......... | A61N 1/36031 |
| 2019/0159675 A1* | 5/2019 | Sengupta | ........... | A61B 5/14553 |

\* cited by examiner

SCREENING OF MALIGNANT GLIOMA, BRAIN TUMORS, AND BRAIN INJURIES USING DISTURBANCE COEFFICIENT, DIFFERENTIAL IMPEDANCES, AND ARTIFICIAL NEURAL NETWORK

CROSS-REFERENCE TO RELATED APPLICATIONS

This application claims the benefit of Provisional Patent Application No. 62/535,445, filed Jul. 21, 2017. The disclosure of U.S. Provisional Patent Application No. 62/535,445 is incorporated herein by reference.

BACKGROUND

The estimated new cancer cases of brain and central nervous system are about 3.5 per 100,000 people worldwide per year. In the United States, there were an estimated 22,620 new cases of malignant primary brain and central nervous system (CNS) tumors in 2013 and about 73.8% are malignant glioma which include glioblastoma, 45.2%, other astrocytoma 17.4%, oligodendrogliomas 5.0%, ependymoma tumor 3.5%, and oligoastrocytoma, 2.7%. The estimated new case number is 23,830 in 2018. The pathology, diagnosis, management and therapy of gliomas are well studied and extensively reported.

The 2007 World Health Organization (WHO) classification of central nervous system tumors includes four grades. While glioblastoma is classified as WHO grade IV, most other astrocytoma, oligodendroglioma, ependymoma, and oligoastrocytoma are classified as WHO II or III. Most malignant glioma, such as glioblastoma and astrocytoma, are very aggressive and average survival time tends to be less than one or two years with limited treatment. Studies have shown that early diagnosis combined with extensive treatment and comprehensive surgery provides a better immediate postoperative performance and longer survival.

Early diagnosis is paramount for effective medical management and surgical intervention. Recent advances in medical imaging technology (CT and MRI) have led to earlier diagnosis of brain tumors, providing oncologists with a greater time window for therapeutic management. Thus, medical imaging techniques have been commonly used for the diagnosis of malignant glioma. However, limited by the accessibility of medical imaging systems and medical facilities, the diagnosis of malignant glioma is often delayed, or as a consequences of incidental findings on the medical images of those with head injuries.

This disclosure describes a system and a method to screen malignant gliomas, other brain tumors, and brain injuries using a disturbance coefficient, differential impedances, and artificial neural networks. The system calculates the disturbance coefficient and differential impedances in a prescribed frequency range. The disturbance coefficient is a weighted coefficient, which includes many factors such as differential impedances using different measurement configurations, etc. The differential impedances include transmission differential impedance and receiving differential impedance with different configurations. The method includes an arrangement to maximize the sensitivity of detecting brain tissue condition. It is achieved by transmitting prescribed electromagnetic waves that propagate through human brain tissue, measuring the differential impedances of brain tissue, and screening malignant glioma, other brain tumor, and brain diseases with a high sensitivity and specificity using an artificial neural network. The method provides an effective and cost effective approach for screening malignant gliomas, other brain tumors, and brain injuries.

SUMMARY

The present disclosure describes methods to screen malignant glioma and brain injury using a noninvasive and cost effective approach. The system implements the methods using a disturbance coefficient, differential impedances in a prescribed frequency range, and artificial neural networks.

One aspect of this present disclosure is a system of noninvasive screening of malignant glioma comprising of switch networks to form different measurement configurations that measure the disturbance coefficient, a signal generator consisting of digital-to-analog convertor (DAC) or direct digital synthesizer (DDS) that generates the prescribed electrical excitation signals, a transmitter circuit that amplifies, filters, and transmits the excitation signals to a brain tissue region, transmission lines with prescribed lengths to transmit and receive the excitation signals from the electrodes or coils that are attached to the head, at least two transmitting electrodes or coils emitting the excitation signal to brain tissue, at least two receiving electrodes or coils located at two sides of the brain tissue detecting the excitation signal that propagates through the brain tissue, at least one differential amplifier that finds the difference of the signals received from two receiving electrodes or coils, a receiver circuit that amplifies, filters, and digitizes the output of the differential amplifiers, analog-to-digital converters (ADC) that converts the output of the receiver circuit, a field programmable gate array (FPGA) that generates excitation signal to DAC and receiving digitized data from ADCs, a FPGA or a microcontroller that configures the switches, programmable potentiometers, and the FPGA for the DAC and the ADC, and other electronic components, and a computer that a computer that generates and transfers control data to FPGA, receives data from ADCs, conducts Fourier transform and spectral analysis, calculates parameters of frequency dispersion and harmonics, calculates receiving differential impedances and transmission differential impedance, calculates the derivatives and statistics of differential impedance, calculates the nonlinearity of the brain tissue, and estimates the disturbance coefficient for screening malignant gliomas, other brain tumors, and brain injuries.

According to another aspect of the disclosure, the system calculates the disturbance coefficient that quantitatively measures the likelihood of the malignant glioma. The disturbance coefficient is a sum of weighted parameters including receiving differential impedances and transmission differential impedances in a prescribed frequency range with different configurations and different excitation signals, frequency dispersions of the differential impedances, harmonics at prescribed frequencies, nonlinearity of brain tissue, measurement distances, measurement configurations, and the sex and age of a patient.

According to another aspect of the disclosure, the system transmits a differential electrical signal to two sides of the human head and detects the induced electric fields at the two sides to obtain transmission differential impedance and receiving differential impedance in a prescribed frequency range with a prescribed excitation signal.

According to another disclosure, the system transmits and receives excitation signals that include sinusoidal signals, tone bursts, pulses, coded pulses, and chirps in a prescribed frequency range to measure the differential impedances, spectral responses, frequency dispersion, harmonic responses, nonlinearity, and disturbance coefficient of brain tissue to indicate the likelihood of malignant gliomas and brain injuries.

According to another disclosure, coded pulses and chirps are received and detected by using digital orthogonal detectors in the computer to obtain differential impedances with minimized effects of multipath, reflections, interference and noise to increase the diagnosing sensitivity of malignant glioma.

According to another disclosure, transmission lines having a prescribed length are selected for a particular frequency of the excitation signal so that the input impedance of the transmission line are at the middle point between the maximum input impedance and the minimum input impedance to maximize the detection sensitivity of brain tissues variation due to malignant glioma, other brain tumors, and brain injuries According to another disclosure, the electrodes or coils are selectively connected to the excitation signal and receiver so the excitation is applied to selected positions on a head skull and detections are done at the selected positions on the brain skull, such as along the squamosal sutures above ears.

According to another disclosure, the received signals are selectively connected to differential amplifier so that the different modes of receiving signals are acquired for calculating the disturbance coefficient.

According to another disclosure, the excitation current meets the safety standards in a prescribed frequency range by automatically and adaptively controlling the amount of the current emitting from a current source according to the operating frequency.

According to another disclosure, the bandwidth of band pass filters in the receivers are automatically and adaptively changed to reduce the noise and interference outside of the prescribed frequency range.

According to another disclosure, the transmission and receiving electrodes or coils are attached to the two sides of a human head along the squamosal sutures above ears for improving the efficiency of the transmission and receiving though brain tissues.

According to another disclosure, the transmission lines connecting the electrodes or coils with the transmitter are selected with prescribed lengths for a prescribed frequency so that the difference of differential impedances between normal brain tissue and malignant gliomas are maximized with prescribed transmitted signals.

According to another disclosure, the transmission lines are selected with prescribed lengths for a prescribed frequency so that the reflection coefficient of the transmission lines has a value that is in the middle region from the minimum to the maximum of the reflection coefficient as the length changes, to maximize the sensitivity of screening malignant glioma.

According to another disclosure, the transmission lines are selected with prescribed lengths for a prescribed frequency so that the input impedance of the transmission lines has a value that is in the fast change region due to the change of input impedance, to maximize the sensitivity of screening malignant glioma.

According to another disclosure, the excitation signal is a sinusoidal that has a frequency selected from a prescribed frequency range.

According to another disclosure, the excitation signal is a pulse or a pulse sequence that has a pulse width and pulse repetition frequency selected from a prescribed range of pulse widths and a prescribed range of the pulse repetition frequencies.

According to another disclosure, the excitation signal is coded signal such as a chirp signal that has a frequency changing with time to acquire tissue responses in a prescribed frequency range and to minimize the interference, multipath effects, and radio frequency (rf) noise and other noise.

According to another disclosure, the high harmonics of the tissue response to the excitation signal are measured to study the nonlinear responses of the malignant glioma, other brain tumors, and brain injury.

According to another disclosure, the frequency dispersion of the tissue response to the excitation signal is measured to study the frequency responses of the malignant glioma, other brain tumors, and brain injury.

According to another disclosure, the disturbance coefficient is a weighted sum of differential impedances and their derivatives, normalized harmonic difference, nonlinearity of tissue frequency response, According to another disclosure, an artificial neural network is trained to estimate the disturbance coefficient for indicate the likelihood of malignant glioma by using clinical data collected by the screening system and pathological information of patients.

According to another disclosure, the disturbance coefficient is analyzed by using the ROC curve for providing a standard as guidance to screen malignant glioma, other brain tumors, and brain injury with a likelihood value based on the sensitivity and specificity.

DETAILED DESCRIPTION

Figure 1:
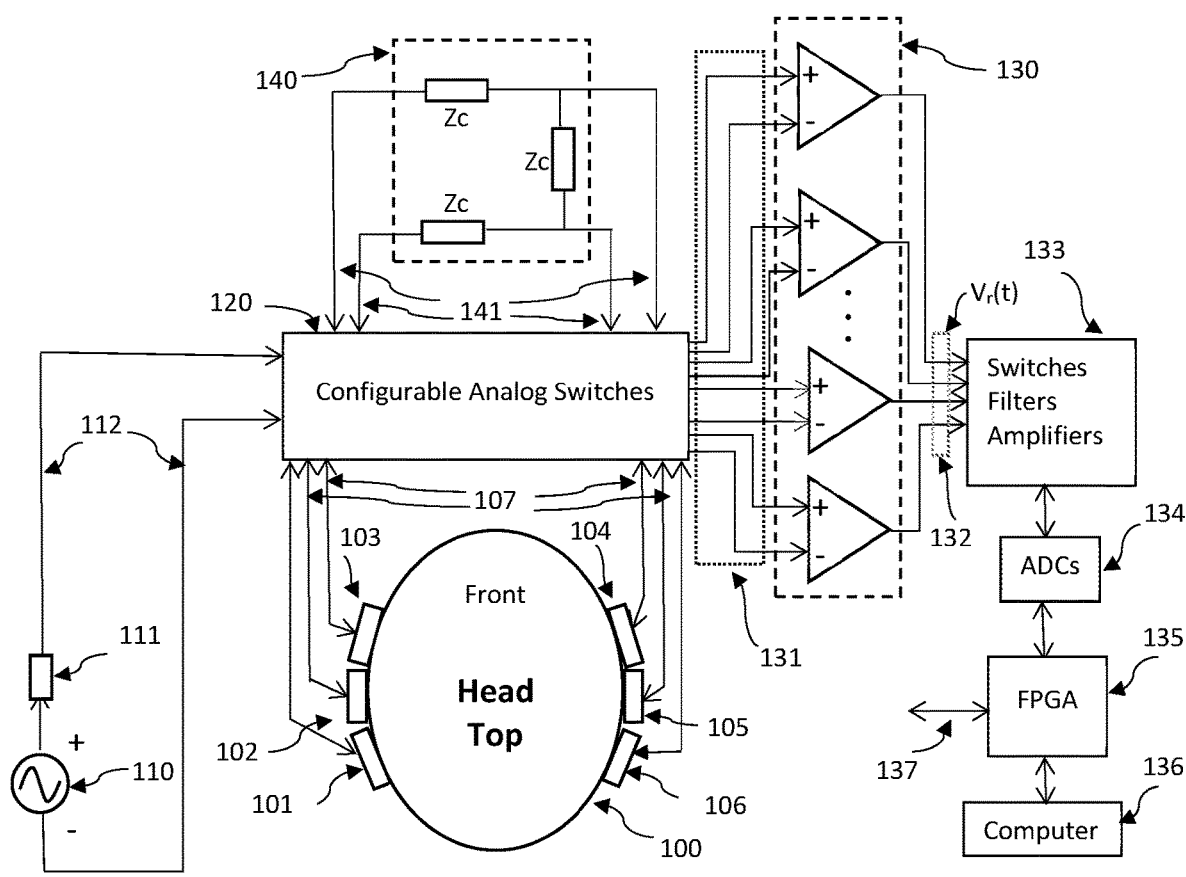
FIG. 1. Shows an example of system block diagram for screening malignant gliomas, other brain tumors and injuries FIG. 2. Shows an example of system setups for measuring receiving differential impedance FIG. 3. Shows an example of system setups for measuring transmission differential impedance FIG. 4. Shows an example of system setups for measuring two channels of receiving differential impedance FIG. 5. Shows an example of system setups for measuring phase difference of two channels FIG. 6. Shows an example of excitation source and controllable differential current source FIG. 7. Shows an example of band pass filter with controllable bandwidth FIG. 8. Shows an example of system calibration using a calibration circuit FIG. 9. Shows an example of binary excitation pulses FIG. 10. Shows an example of the spectral distribution of binary excitation pulses FIG. 11. Shows an example of sinusoidal excitation, spectral distribution of linear response of tissue, and spectral distribution of nonlinear response of tissue FIG. 12. Shows an example of tone burst excitation signal FIG. 13. Shows an example of chirp excitation signal FIG. 14. Shows an example of system setup using 12 electrodes around a head FIG. 15. Shows an example of neural network setup for screening malignant gliomas and brain injuries using an artificial neural network FIG. 16. Shows an example of the disturbance coefficients of malignant glioma compare with the average disturbance coefficient of people without brain glioma FIG. 17. Shows an example of ROC curve using the disturbance coefficient for screening malignant glioma FIG. 18. Shows an example of cascaded neural network for screening malignant glioma FIG. 19. Shows an example of ROC curves of training results and validation results using leave-one-out validation for screening malignant glioma FIG. 20. Shows an example of transmission line with a load impedance and an input impedance FIG. 21. Shows an example of the magnitude of the input impedance of a transmission line as a function of the length of the transmission line.

An example of the system measuring the disturbance coefficients and electrical differential impedances is shown in FIG. 1, where excitation source 110 generates a prescribed electrical excitation signal, current sensor 111 measures the current transmitted to head 100 via transmission lines 112, 107 and transmission electrodes or coils or other forms of transmitters selected from 101 to 106 using switches 120, the inputs of differential amplifiers 130 are connected to receive electrodes or coils or other forms of receivers selected from 101 to 106 using switches 120 and transmission lines 131, 107, calibration circuit 140 is connected to transmission line 112 and 131 via switch 120 during a calibration process to determine the values of the differential impedances, signal conditioning unit 133 includes switches, filters, and amplifiers, to process selected outputs 132 of differential amplifiers 130, analog-to-digital convertor (ADC) 134 digitizes the outputs of signal conditioning unit 133, field-programmable gate array (FPGA) 135 processes the digitized samples from ADC 134 and transfers the results to computer 136 for display, analysis, and archiving, FPGA 135 also provides required data for DAC or DDS in signal source 110 and also provides control signals for controlling switches and other devices.

Switches 120 and switches in signal conditioning unit 133 are multipath switch arrays that allow different configurations to connect between transmission lines 112 and 131 to electrodes or coils or other forms of transmitter and receivers from 101 to 105. Using the switches, different configurations of the system can be achieved, such as the examples shown in FIGS. 2, 3, 4, 5, and 8. The switches are controlled by FPGA 135 and computer 136, according to the measurement configurations required to calculate the disturbance coefficient.

Figure 2:
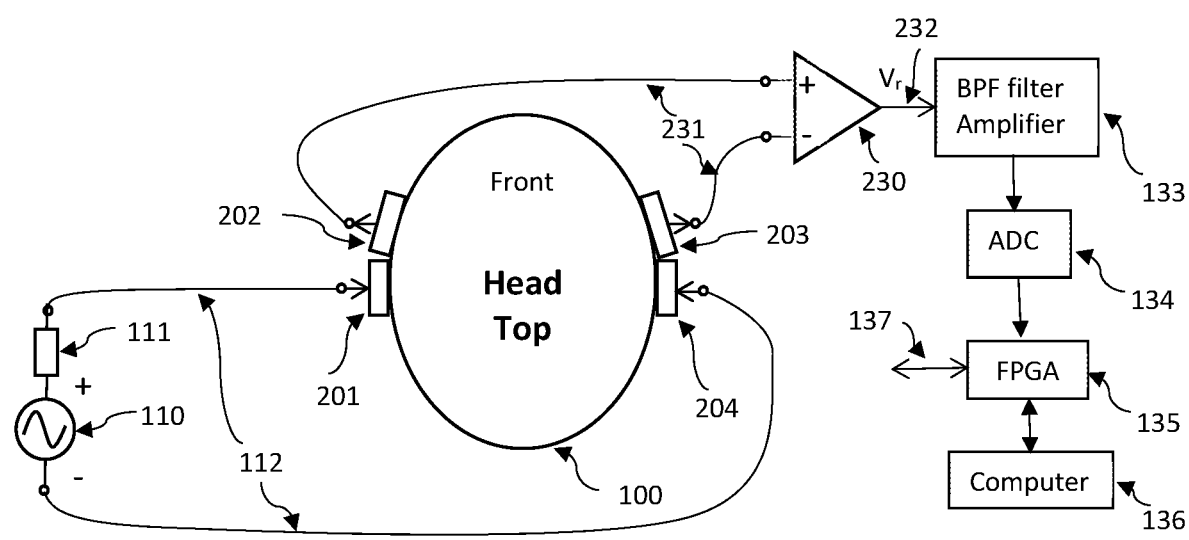

An example of a configuration shown in FIG. 2 provides a measurement defined as "receiving differential impedance" where the differential signal is applied to transmitters 201 and 204, and the receiving differential amplifier is connected to receivers 202 and 203. The receiving differential impedance measures internal tissue condition with minimized impact from skin, electrodes, power lines, and other common noises.

Figure 3:
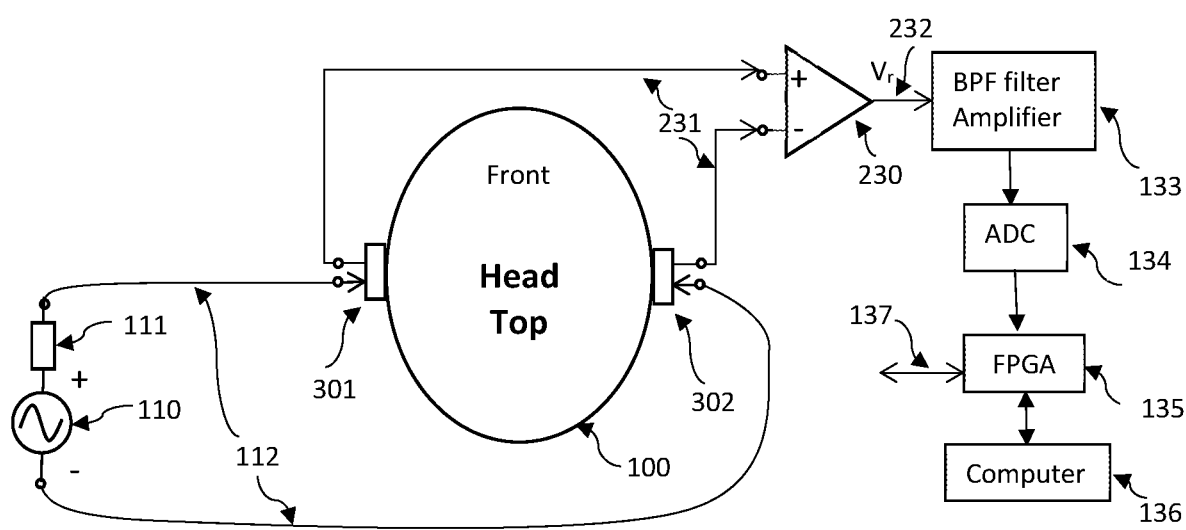

An example of a configuration shown in FIG. 3 provides another measurement called "transmission differential impedance", where the receivers and transmitters are connected together at 301 and 302, respectively. Transmission differential impedance measures total cross impedance with minimized common noise such as power lines etc. It provides some indication of the skin and electrode conditions, as well as the tissue condition.

Figure 4:
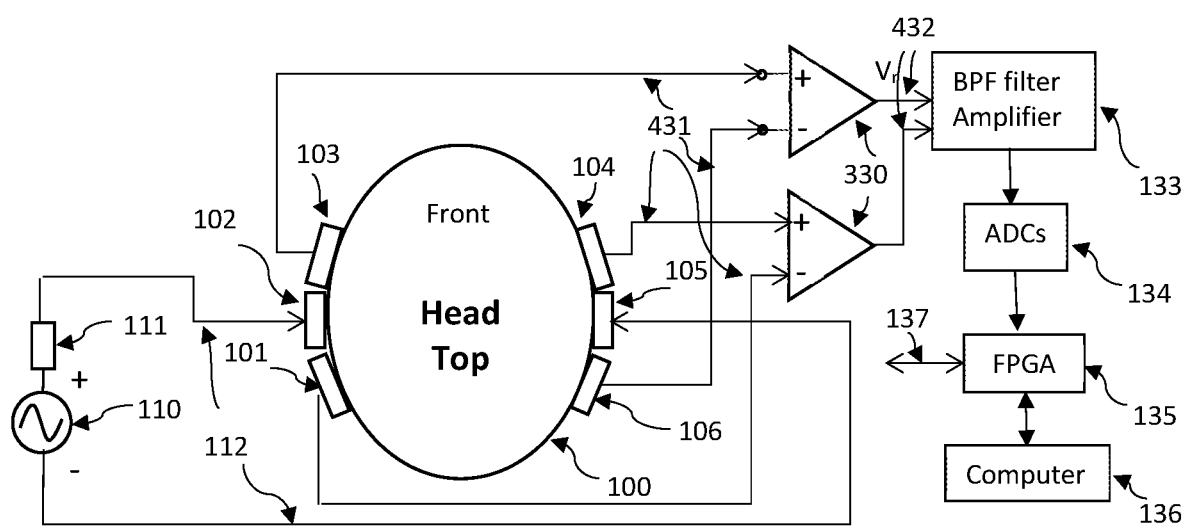

An example of a configuration shown in FIG. 4 measures two receiving differential impedances at different locations.

Figure 5:
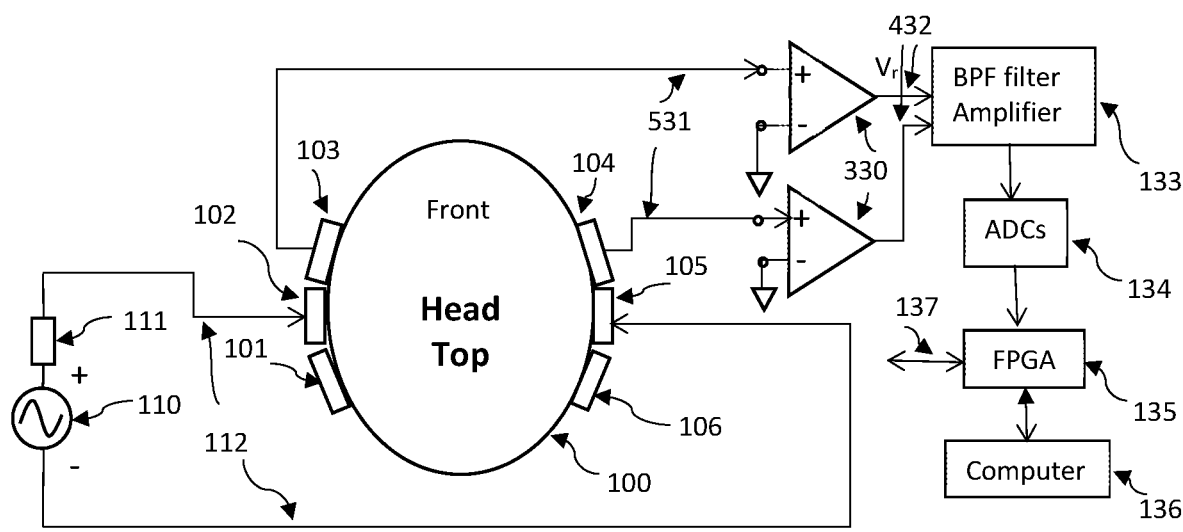

An example of a configuration shown in FIG. 5 measures impedances at two locations so that the true phase difference between two locations can be obtained by FPGA 135 or computer 136.

The positions of the transmitter and receivers can be exchanged or selected among available electrodes or coils or other forms of transmitters and receivers, according to the needs of the algorithms to calculate the disturbance coefficient. The connections between the receivers and receiving differential amplifiers can also be configured and changed according to the algorithm to calculate the disturbance coefficient.

Figure 6:
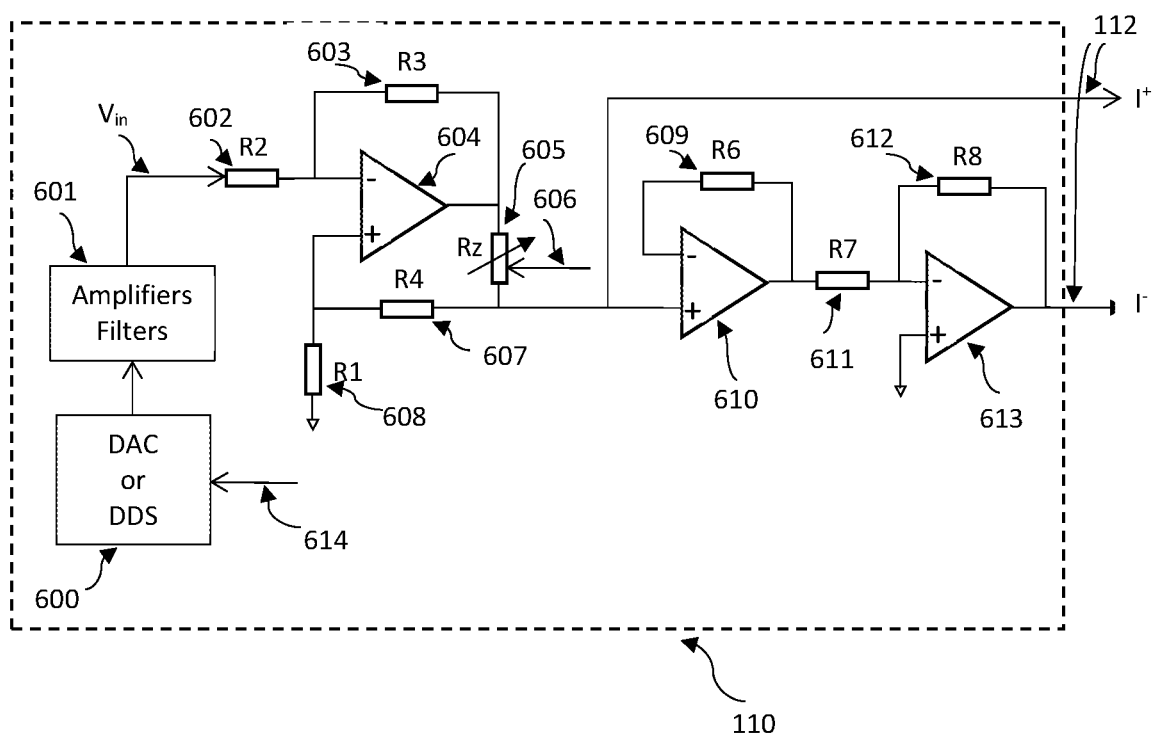

An example of excitation source 110 is shown in FIG. 6, which includes a signal generator 600 that is either a direct digital synthesis (DDS) device or a digital-to-analog convertor (DAC) driven by FPGA 135, filters (such as band pass filters), amplifiers, and a differential current source. The DAC or DDS uses digital data from FPGA 135 to generate the excitation signal. The data and control signals such as clock and triggering signals from FPGA 135 are transferred through data lines 614 to signal generator 600. The excitation signal generated by 600 is conditioned by filters and amplifiers. A controllable differential current source is shown in FIG. 6, which includes three amplifiers 604, 610, and 613, seven resistors (R1, R2, R3, R4, R6, R7, R8), and an electronically controllable potentiometer Rz 605. Components 602, 603, 604, 605, 607, 608 form a single-ended current source. A ratio between the output of the signal conditioner 601 and the resistance value of Rz 605 determines the current value of the current source 100, $I+ = V_{in}/R_z$. The potentiometer Rz is digitally configured for a prescribed resistance according to a prescribed frequency by using the control commands from lines 606 that are connected with FPGA 135. Components 610 and 609 provide buffer and isolation. Components 611, 612, and 613 form an inverter that provide a negative reference for the current source. As the I+ and I− are applied to a load, the current between I+ and I− is regulated by the single-ended current source which is $V_{in}/R_z$. FIG. 6 shows the controllable differential current source that enables a configuration to prevent the common noise and interference to enter the system.

The variable current source using Rz 605 is important as the disturbance coefficient uses differential impedances measured in a wide frequency range such as from 1 Hz to 2 MHz. According to the safety standard for allowable current emitting to a human body, the current limitation is different for a different frequency range. In general, the limitation is lower for lower frequency. If the current source produce a constant current for all frequencies, the current must be very low such as less than 100 μA. As the high frequency is highly attenuated in human tissue, a higher current is needed for a higher frequency. Thus, a current source is needed to produce different amount of current for different frequencies. Rz 605 is introduced to achieve the variable current by using a potentiometer that can be electronically configured and controlled by a FPGA.

Figure 7:
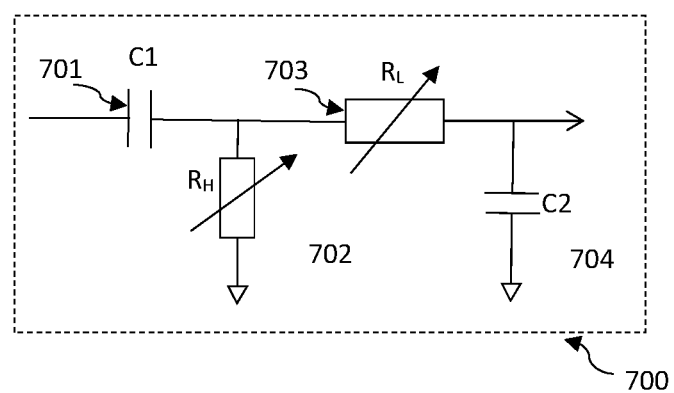

An example of an electronically tunable band pass filter is shown in FIG. 7. The electronically configurable potentiometers 702 and 703 are used to obtain tunable bandpass filter 700. Capacitor C1 701 and resistor $R_H$ 702 form a high pass filter whose corner frequency is determined by the capacitance and the resistance. As the resistance of $R_H$ 702 is electronically changeable, the corner frequency is also changeable according to the need. In a similar situation, the potentiometer $R_L$ 703 is used to tune the corner frequency of the low pass filter formed by C2 704 and $R_L$ 703. Thus, the bandwidth of the bandpass filter shown in FIG. 7 can be tuned according to a prescribed frequency for the needs of the algorithm to calculate the disturbance coefficient.

Figure 8:
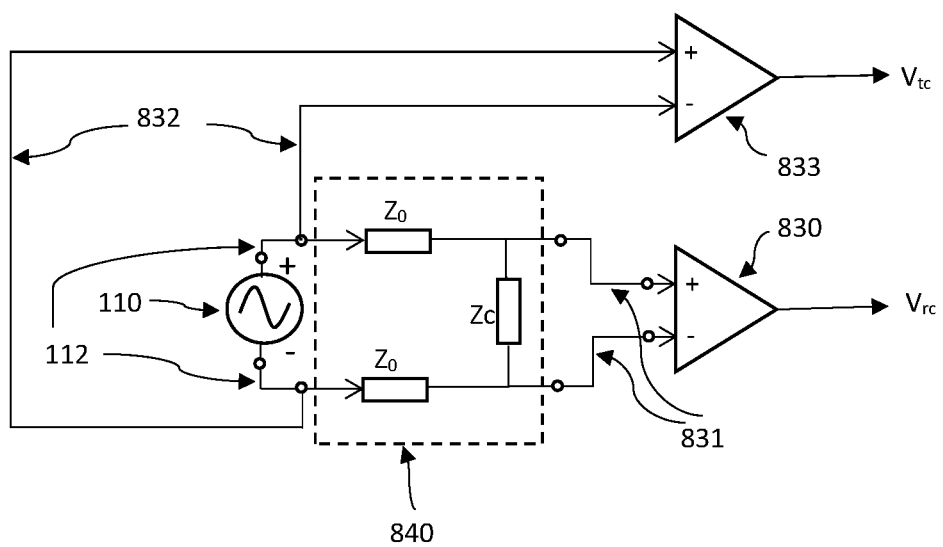

An example of determining the values of the differential impedance is the calibration shown in FIG. 8 where the excitation source is applied to the impedance network via transmission line 112 and switch 120, the inputs of receiving differential amplifiers 830 and 833 are connected to receiving terminals of the impedance network via transmission lines 831 and 832 using switches in signal conditioning unit 133.

If the excitation signal is a current source emitting current $I_0$, and the receiving voltage $V_r$ at the output of the differential amplifier as shown in FIG. 3 when the brain tissue is measured, the transmission differential impedance is:

$$Z_d = \frac{V_r}{GI_0} \quad (1)$$

where G is the gain of the differential amplifier, the current $I_0$ can be obtained by the current sensing circuit 108.

If the configuration of FIG. 2 is used, the receiving differential impedance is obtained:

$$Z_r = \frac{V_r}{GC_r I_0} \quad (2)$$

where $C_r I_0$ is the current between receivers 202 and 203. $C_r$ is between 0 to 1, but it is unknown. One may let $C_r$ be a constant so that (2) provides a relative measurement of receiving differential impedance. The following procedure allows a more precise estimation of receiving impedance.

The measurements of transmission and receiving impedance can be obtained by using a calibration method. As show in FIG. 8, the impedance values of $Z_0$ and $Z_c$ are known; thus, their measurements $V_{tc}$ and $V_{rc}$ can be used to calibrate the transmission and receiving impedances of brain tissue. The total impedance, $$Z_{d0} = 2Z_0 + Z_c \quad (3)$$

can be used to calibrate the transmission impedance of brain-tissue, $$Z_t = Z_{d0} \frac{V_r}{V_{tc}} \quad (4)$$

where $V_{tc}$ is the output of the of the differential amplifier shown in FIG. 8, $V_r$ is the output of the differential amplifier as shown in FIG. 3. Similarly, the receiving differential impedance of brain tissue is, $$Z_r = Z_c \frac{V_r}{V_{rc}} \quad (5)$$

where $V_{rc}$ is the output of the of the differential amplifier for the calibration circuit in FIG. 8, $V_r$ is the output of the differential amplifier output for measuring brain tissue as shown in FIG. 2. Note that the values of all impedances used in the equations (3), (4) and (5) are complex.

When the system is applied to a human head, the impedance measurements at one location includes some interferences. The interferences include radiation from AC power lines, electrode conditions, skin conditions, and radio frequency (rf) radiations. In order to only measure the brain tissue condition, we measure the difference of the impedances at multiple locations on the head using different configurations. Both transmission and receiving differential impedances have high rejection capability for common noises from AC power line and RF interferences.

Besides the high rejection capability for the common noises, the receiving differential impedance has the capability of reducing the effects of skin and electrodes. It measures the difference of impedances between two points; thus, it is mostly dependent on the tissue inside of a human head, and relatively independent of the type of electrode, skin conditions, electronic circuit layouts, and radiation of AC power lines and rf interference.

Transmission differential impedance provides an overall indication of the tissue, skin, and electrodes, as it measures the total cross impedance between two points. When a differential current source is used as the excitation source, the current with a set amount is emitted regardless of the load condition. But in reality, the current may be decreased somewhat due to a very high impedance value of a load. If the skin and electrode create a very high impedance condition, the receiving differential impedance would be impacted. Thus, the measurement of transmission impedance provides a reference to indicate the condition and to correct the receiving differential impedance.

The skin and electrode conditions can be further monitored by using the current sensor 111. The measurement of 111 can be used to correct the differential impedances based on equations (1) to (5):

$$Z = Z_m \frac{I_0}{I_1} \quad (6)$$

where $Z_m$ is a measured impedance, $I_0$ is measured by the current sensor when the transmission differential impedance is not very high, and $I_1$ is measured by the current sensor when the impedance is very high.

Figure 9:
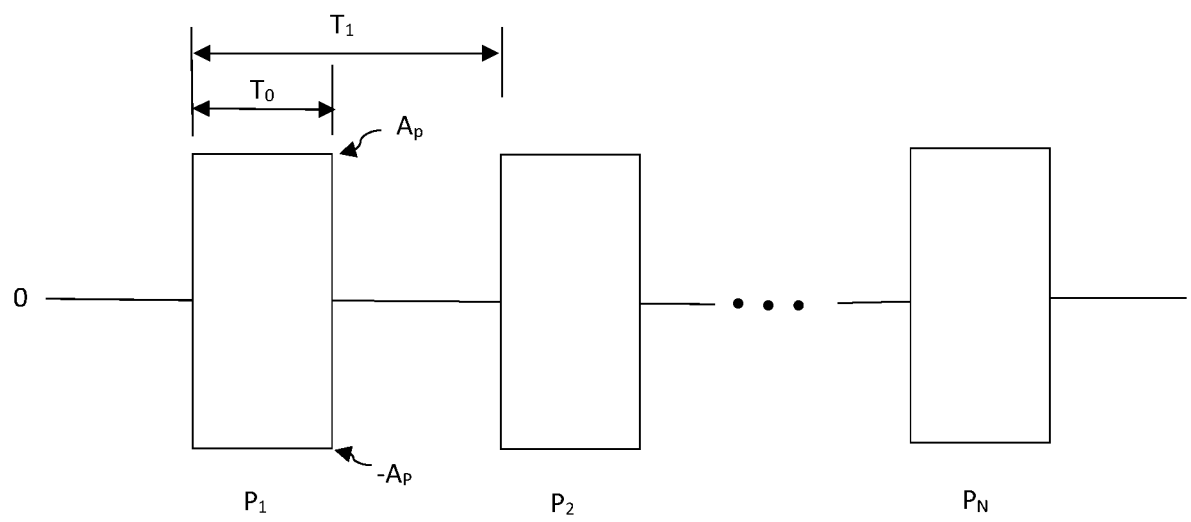

The differential excitation source may be a sinusoidal, pulses, coded pulses, chirps, etc. FIG. 9 shows a sequence of differential binary pulses that have a pulse width of $T_0$ and a pulse period of $T_1$. A prescribed pulse width allows a study of tissue response in a prescribed frequency range. The reliability of the measured differential impedances increase as the number of the pulses increases.

When single pulse with a long pulse width is used for the excitation signal, tissue response to a very low frequency range is investigated.

Figure 10:
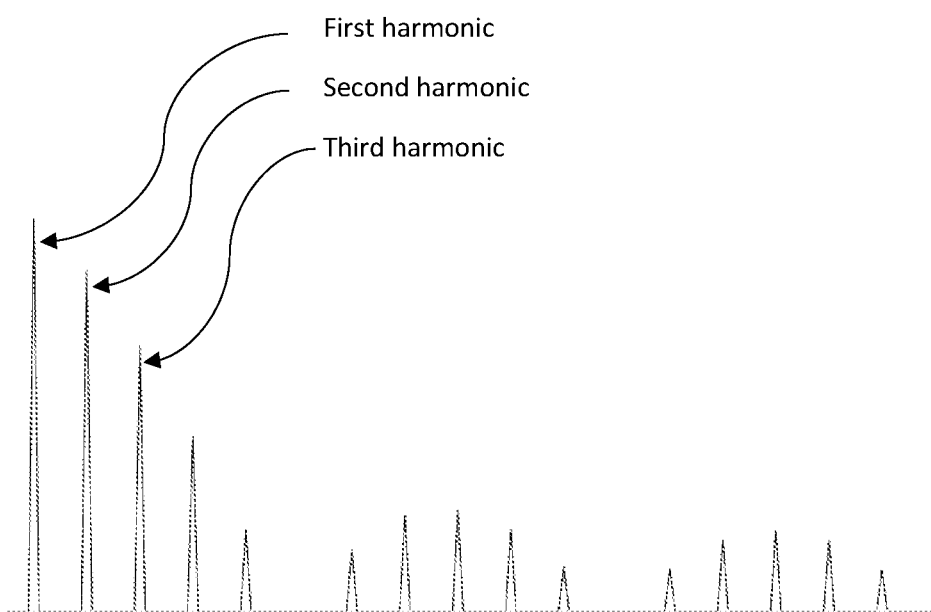

The Fourier analysis of the output of the receiving differential amplifier provides frequency dispersion property of the brain tissue, malignant glioma, other brain tumor, and brain injury, $$V_r(\omega) = \int v_r(t) e^{-j\omega t} dt = M(\omega) e^{j\theta(\omega)} \quad (7)$$

where $M(\omega)$ and $\theta(\omega)$ are magnitude and phase of output $v_r(t)$ 132 of the receiving differential amplifier. One of the spectral distribution of tissue response to the pulse sequence of FIG. 9 is illustrated in FIG. 10. The frequency dispersion of tissue condition can be partially described by the normalized differences between different harmonics which are defined as, $$\Delta M_1 = (M(\omega_1) - M(\omega_2))/M(\omega_1) \quad (8)$$

$$\Delta M_2 = (M(\omega_1) - M(\omega_3))/M(\omega_1) \quad (9)$$

where $M(\omega_1)$ is the magnitude of the first harmonic of the Fourier transform of the sampled measurement of V(t) shown in FIG. 2 and FIG. 3, $M(\omega_2)$ and $M(\omega_3)$ are for the second and third harmonics, etc. Normalized phase harmonic differences are defined as, $$\Delta\theta_1 = \theta(\omega_2) - \theta(\omega_1) \quad (10)$$

$$\Delta\theta_2 = \theta(\omega_3) - \theta(\omega_1) \quad (11)$$

The above equations that measure the frequency dispersion using the harmonic difference can also be used for measuring the nonlinear response of brain tissue including brain tumors and injuries. When a sinusoidal signal having a significant time period is transmitted to brain tissue, the nonlinear response of the tissue is represented in high harmonics. These harmonics are at the locations of multiple integers of the frequency of the sinusoidal signal, not at the frequency locations caused by the finite time periods. When the nonlinearity of tissue is measured by using the single frequency sinusoidal excitation signal and equations (7) to (11), symbol of $\Delta M_1$, $\Delta M_2$, $\Delta\theta_1$, $\Delta\theta_2$ are replaced by $\Delta M_{n1}$, $\Delta M_{n2}$, $\Delta\theta_{n1}$, $\Delta\theta_{n2}$.

Figure 11:
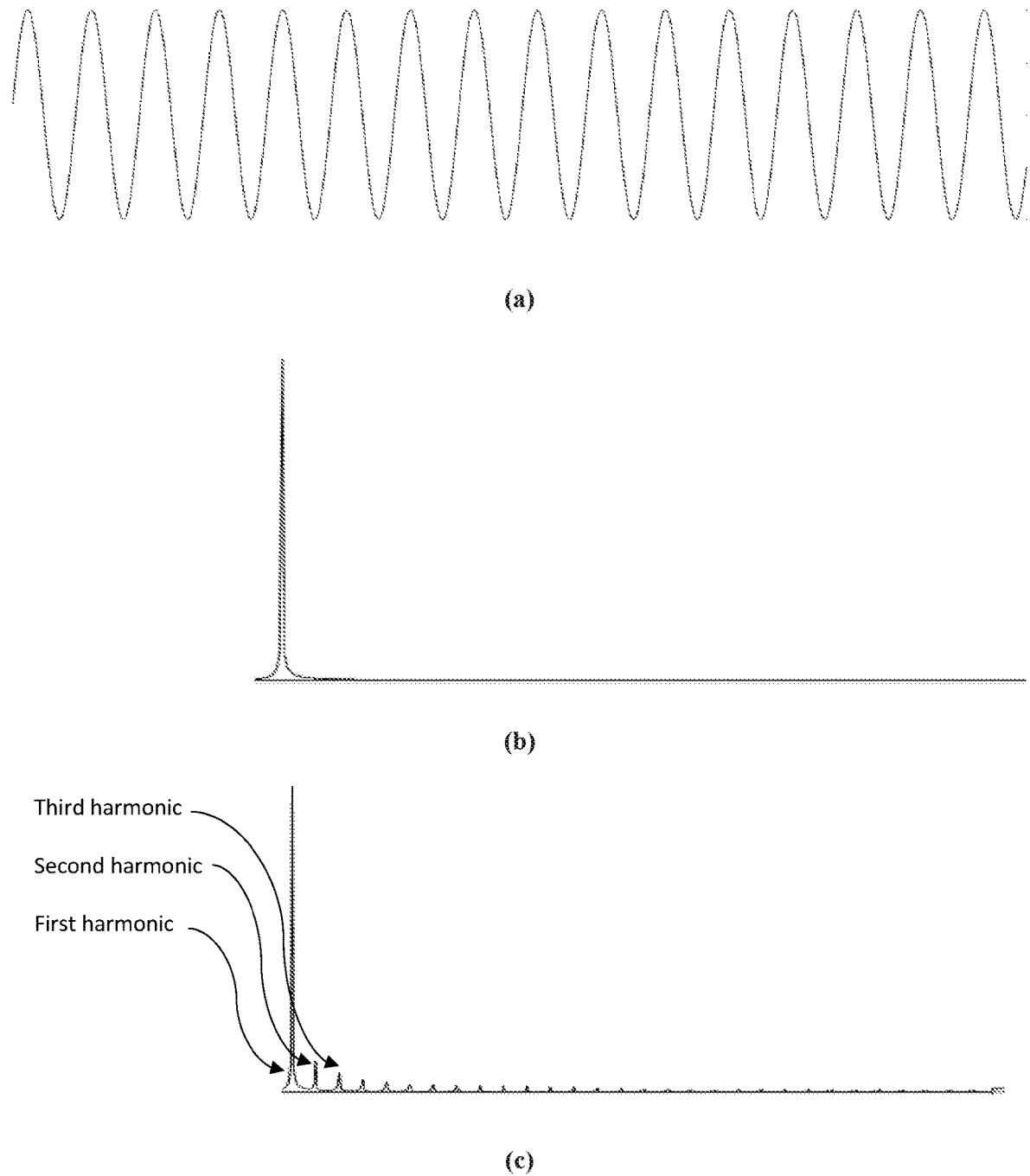

Many prior studies found that different biological tissues have different electrical properties at different frequencies, meaning that the frequency dispersion is different for different biological tissues. Thus, frequency dispersion is utilized to characterize the tissue. In general, the frequency range is from 1 Hz to 2 MHz. Frequencies in tens or hundreds of MHz range are also interested to get the full frequency response of the brain tissue As example shown in FIG. 11, the received signal induced by a sinusoidal excitation signal is shown in (a), the spectral distribution of the received signal from a linear tissue is shown in (b), and the spectral distribution of the received signal including the nonlinear response of the tissue is shown in (c). The harmonics besides the first harmonic are induced by the nonlinearity of tissue. Equation (7) to (11) can be applied to measure the nonlinearity when the excitation signal is a sinusoidal signal which has many cycles at a single frequency. The nonlinearity of tissue response is measured by harmonics using (7) to (11), which are used to screen malignant glioma, other brain tumors, and brain injuries.

Figure 12:
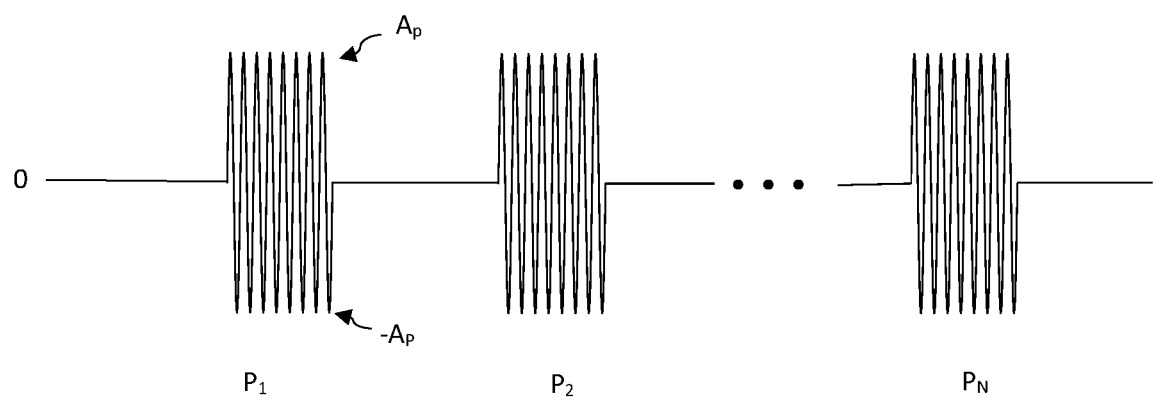

As example shown in FIG. 12, the excitation signal can be a sequence of tone bursts. The center frequency of the sinusoidal burst, the tone burst length, and the burst repetition frequency are prescribed according to the algorithm for the screening.

Figure 13:
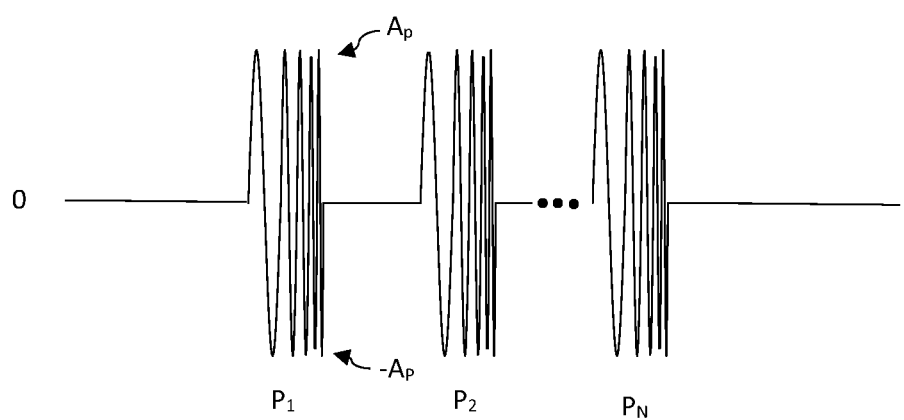

When coded pulses are used for the excitation signal, the interference and multipath impact are reduced to increase the screening sensitivity by using the matching code at the receiver. An example of coded pulse sequence c(t) is the sequence of chirp signal, as illustrated in FIG. 13, where the frequency of the sinusoidal signal increases as the time increases. The shape of the chirp determines the frequency range for the screening. An orthogonal detector is used to process the digitized $v_r(t)$ 132, $$V_r(\omega) = \int_0^T v_r(t) c(t) dt \quad (12)$$

where c(t) is a chirp signal shown in FIG. 13, $v_r(t)$ is an output of the receiving differential amplifier, and T is the total length of the chirp. Any received signal due to multipath delay, reflections, and noise will be reduced by the orthogonal detection, which is digitally implemented in FPGA 135 or computer 136.

Figure 14:
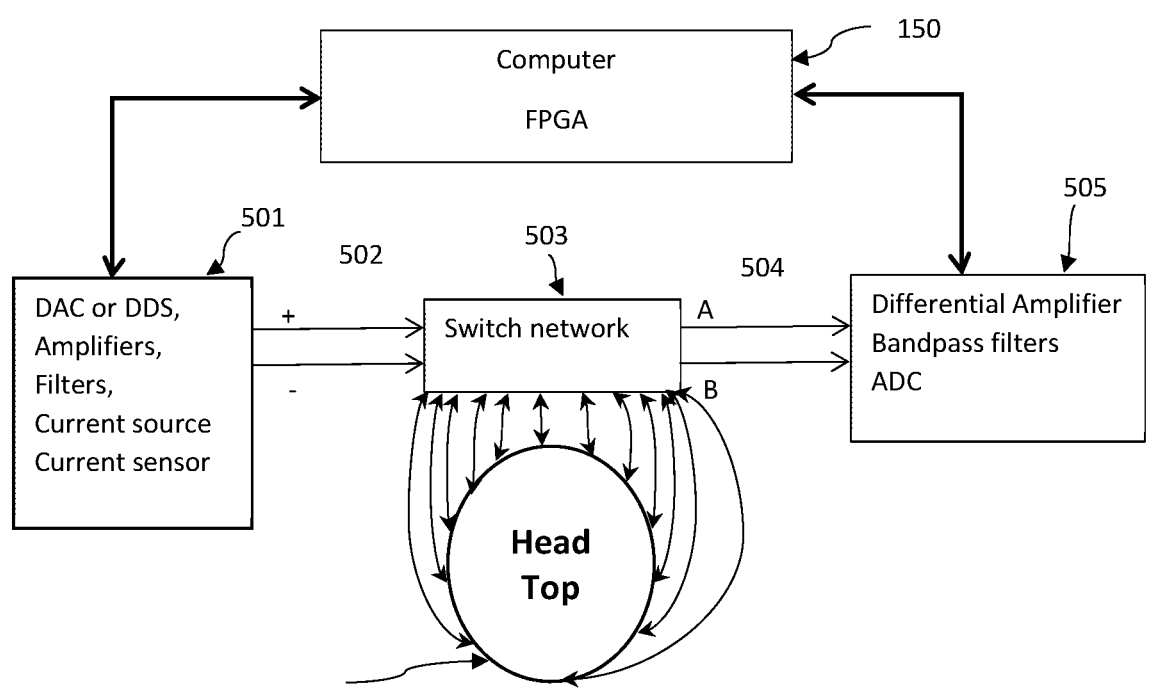

The number of electrodes for the transmitting excitation signal and the receiving tissue response can be significantly larger than the minimum of 4 for the differential impedance measurement, as shown in FIG. 14. The electrodes or other forms of transmitters can be applied to the head as needed by the algorithm of the screening. FIG. 14 shows twelve electrodes or coils and each of them can be connected to any of the transmitters and receivers. The multiple electrodes or coils at different positions provide additional information about the brain conditions. The switch network allows flexible configurations of measurements.

A disturbance coefficient is defined to quantitatively screen malignant glioma, other brain tumors, and brain injuries:

$$D = \sum_{i=1}^{M} a_i Z_r(\omega_i) + \sum_{i=1}^{M} b_i Z_t(\omega_i) + \sum_{i=1}^{M} c_i \Phi_r(\omega_i) + \sum_{i=1}^{M} d_i \Phi_t(\omega_i) + \sum_{i}^{M} e_i \frac{dZ_r(\omega_i)}{d\omega} + \sum_{i}^{M} f_i \frac{d\Phi_r(\omega_i)}{d\omega} + \sum_{i=1}^{M} g_i \frac{Z_r(\omega_i)}{Z_t(\omega_i)} + \sum_{i=1}^{N} h_i \Delta M_i + \sum_{i=1}^{N} o_i \Delta\theta_i + \sum_{i=1}^{L} p_i \Delta M_{ni} + \sum_{i=1}^{L} q_i \Delta\theta_{ni} + \text{other factors} \quad (13)$$

where
1. M is a number of frequencies selected for analysis, N is a number of harmonics for frequency dispersion analysis, L is a number of harmonics for nonlinearity analysis
2. Weighting constants $a_i$, $b_i$, $c_i$, $d_i$, $e_i$, $f_i$, $g_i$, $h_i$, $o_i$, $p_i$, $q_i$, $w_i$, $v_i$ are estimated by data analysis or artificial neural network for screening malignant glioma, other brain tumors, and brain injuries.
3. $Z_r(\omega_i)$ and $\Phi_r(\omega_i)$ are magnitude and phase of receiving differential impedance at frequency $\omega_i$, the excitation signals include pulses, sinusoidal signals, chirps, tone burst, etc.
4. $Z_t(\omega_i)$ and $\Phi_t(\omega_i)$ are magnitude and phase of transmission differential impedance at frequency $\omega_i$, the excitation signals include pulses, sinusoidal signals, chirps, tone burst, etc.
5.

$$\frac{dZ_r(\omega_i)}{d\omega} \text{ and } \frac{d\Phi_r(\omega_i)}{d\omega}$$

are derivatives of the magnitude and phase of receiving differential impedance at frequency $\omega_i$.

6. $\Delta M_i$ and $\Delta\theta_i$ are normalized magnitude difference and phase difference at frequency $\omega_i$ to measure the frequency dispersion using a pulse sequence and equations (7) to (11).
7. $\Delta M_{ni}$ and $\Delta\theta_{ni}$ are normalized magnitude difference and phase difference at frequency $\omega_i$ to measure the nonlinearity of tissue using a continuous sinusoidal signal and equations (7) to (11).
8. Other factors may include medical diagnostic information (such as blood tests and medical imaging information, and other pathological information), head circumference, the direct distance from one side of a head to another side, skin condition, age, sex, etc.

Once the disturbance coefficients are calculated from the data collected from patients with and without malignant glioma, other brain tumors, or brain injuries, an ROC curve is made and a standard can be provided as guidance to screen malignant glioma and other brain injuries with quantitative values of sensitivity and specificity.

The disturbance coefficient defined by equation (13) represents a linear relationship between the inputs and the outputs. The nonlinear mapping between the inputs and outputs provides a broader generalization for the disturbance coefficient to differentiate the malignant glioma, other brain tumors, and brain injuries from patients; thus, a more general description of the disturbance coefficient is:

$$D = f\left(Z_r(\omega_i), Z_t(\omega_i), \Phi_r(\omega_i), \Phi_t(\omega_i), \frac{dZ_r(\omega_i)}{d\omega}, \frac{d\Phi_r(\omega_i)}{d\omega}, \frac{Z_r(\omega_i)}{Z_t(\omega_i)}, h_i\Delta M_j, o_i\Delta\theta_j, p_i\Delta M_{nk} q_i\Delta\theta_{nk}, \text{other factors}\right) \quad (14)$$

where i=1, 2, 3 . . . , M; j=1, 2, 3 . . . , N; k=1, 2, 3 . . . L. The function f( ) is a nonlinear function that maps the measurements and input parameters to the disturbance coefficient to increase the sensitivity and specificity of the screening.

Figure 15:
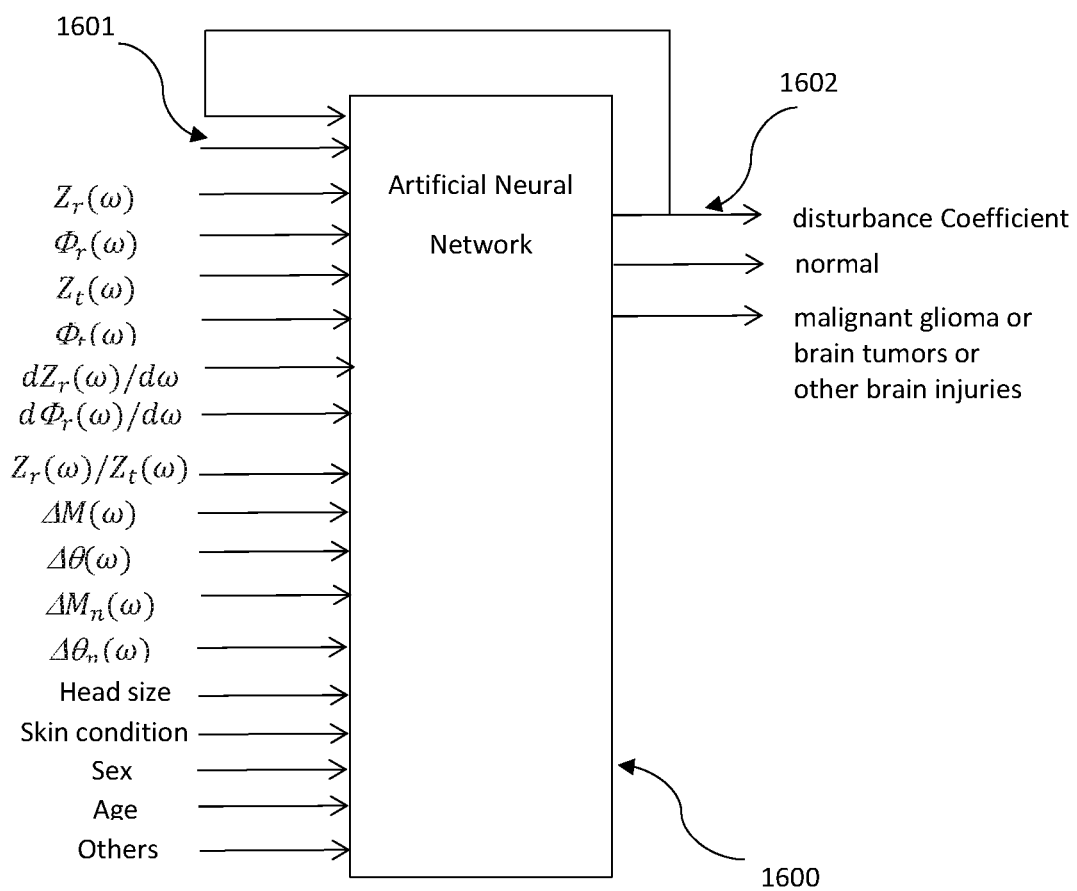

The estimation of the disturbance coefficient involve extensive data analysis using a large amount of data that have high dimensions. This work can also be done by using an artificial neural network. An artificial neural network 1600 to estimate disturbance coefficient is shown in FIG. 15. The inputs of the network include those in equation (13). Each input line 1601 may include multiple inputs. For example, $Z_r(\omega)$ may include 30 magnitudes of differential impedances at 30 different frequencies. $Z_r(\omega)$ may also include the measurements using pulses, tone bursts, chirps, etc. Thus, input 1601 may include hundreds of measurements and the total input of the neural network may include thousands of measurements and their derivatives. On the other hand, the input number can be small if the receiving differential impedances are only used. The neural network for screening malignant glioma, other brain tumors, and brain injury allows an adaptive size of inputs.

During the training process, target values should be provided. The target values for normal and abnormal (malignant gliomas, other brain tumors, and brain injuries) are either 0 or 1. The target values for the disturbance coefficient are estimated from clinical data such as pathological results, tumor size on medical images, bleeding volume, edema volume, etc. The disturbance coefficient is used as an input as well as an output; thus, a recurrence network is used.

The artificial neural network learns from available data to produce outputs that match with the given data with the known outcomes (normal or malignant glioma or other brain injuries). Once the neural network is trained, it can be used to estimate the likelihood of normal and malignant glioma or other brain tumor or brain injuries with given measurements of a person under examination. The neural network continues to learn with new data.

Figure 16:
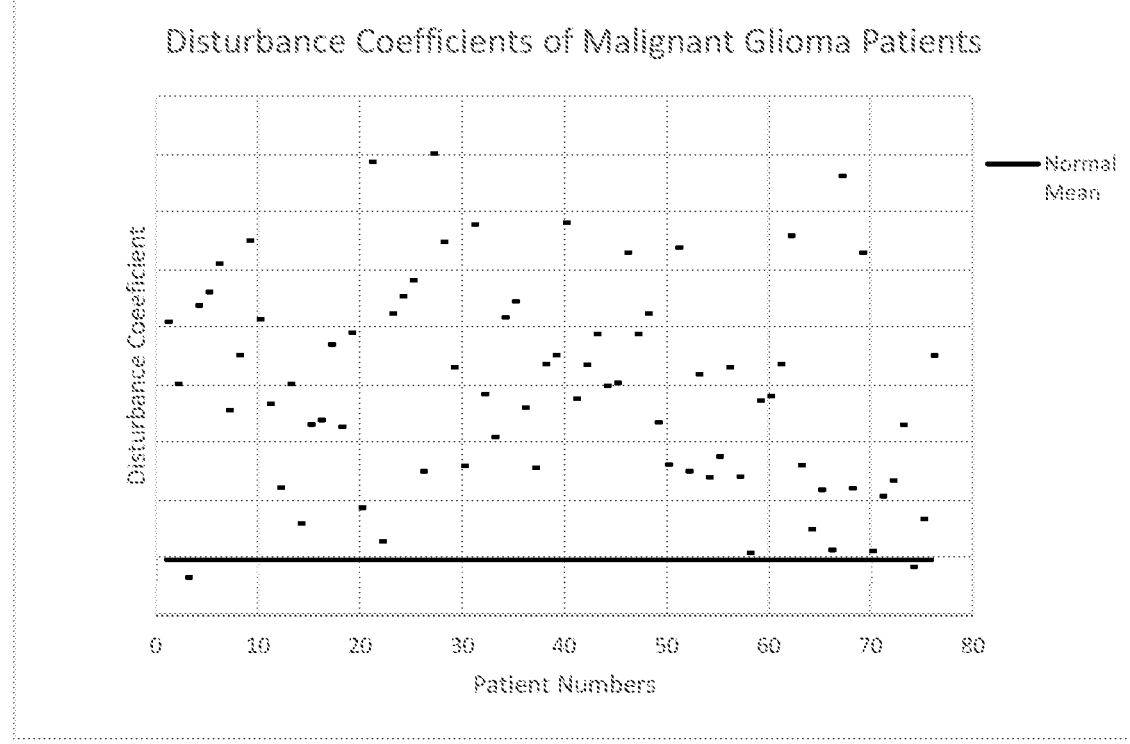

As example shown in FIG. 16, most disturbance coefficients of malignant glioma patients are above the average value of disturbance coefficients of normal people (without malignant glioma, other brain tumor, and brain injuries). The horizontal line represents the average disturbance coefficient of normal people.

Figure 17:
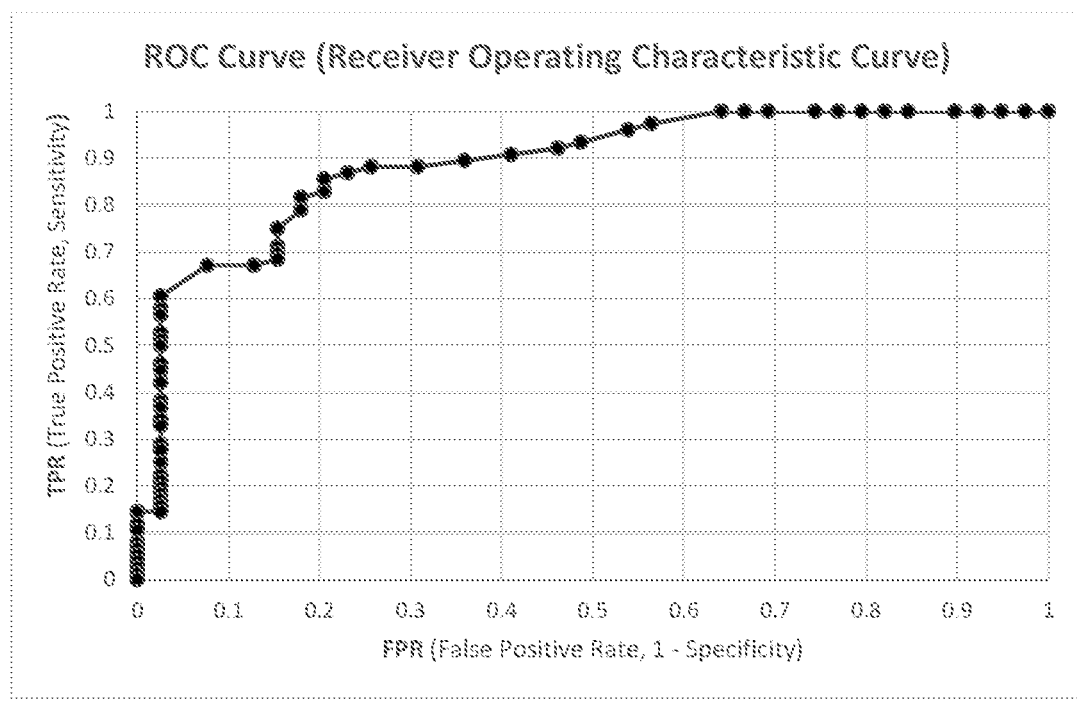

The Receiver Operating Characteristic (ROC) curve of using the disturbance coefficient for the screening is shown in FIG. 17. It shows that the sensitivity is about 85% while as the specificity is about 80/%.

Figure 18:
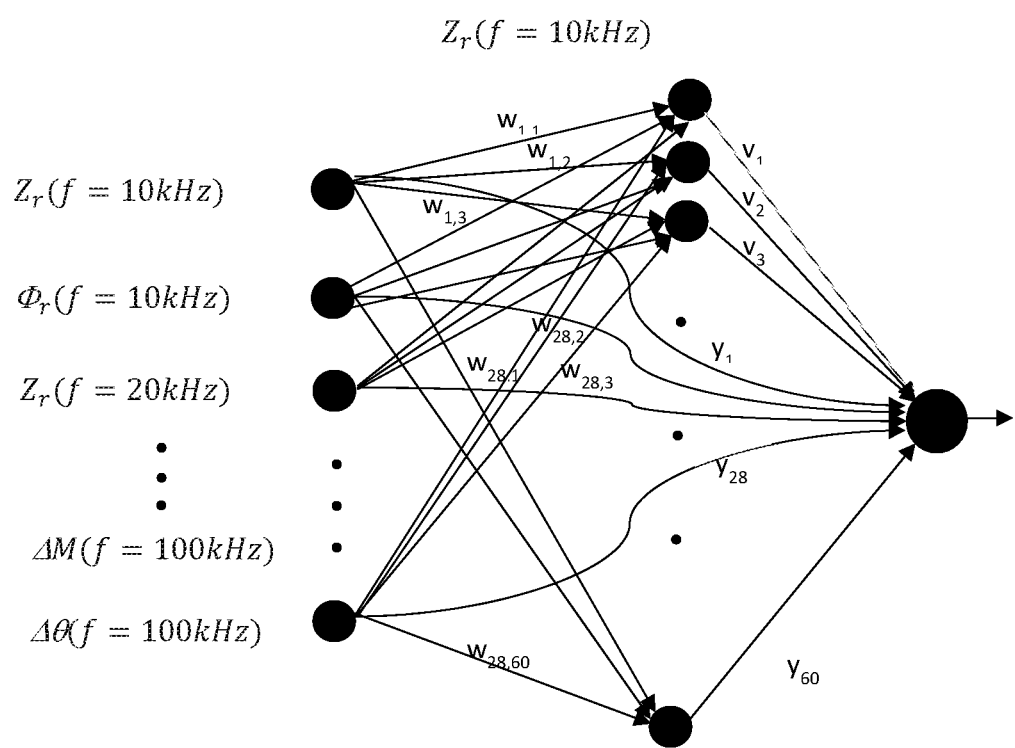
Figure 19:
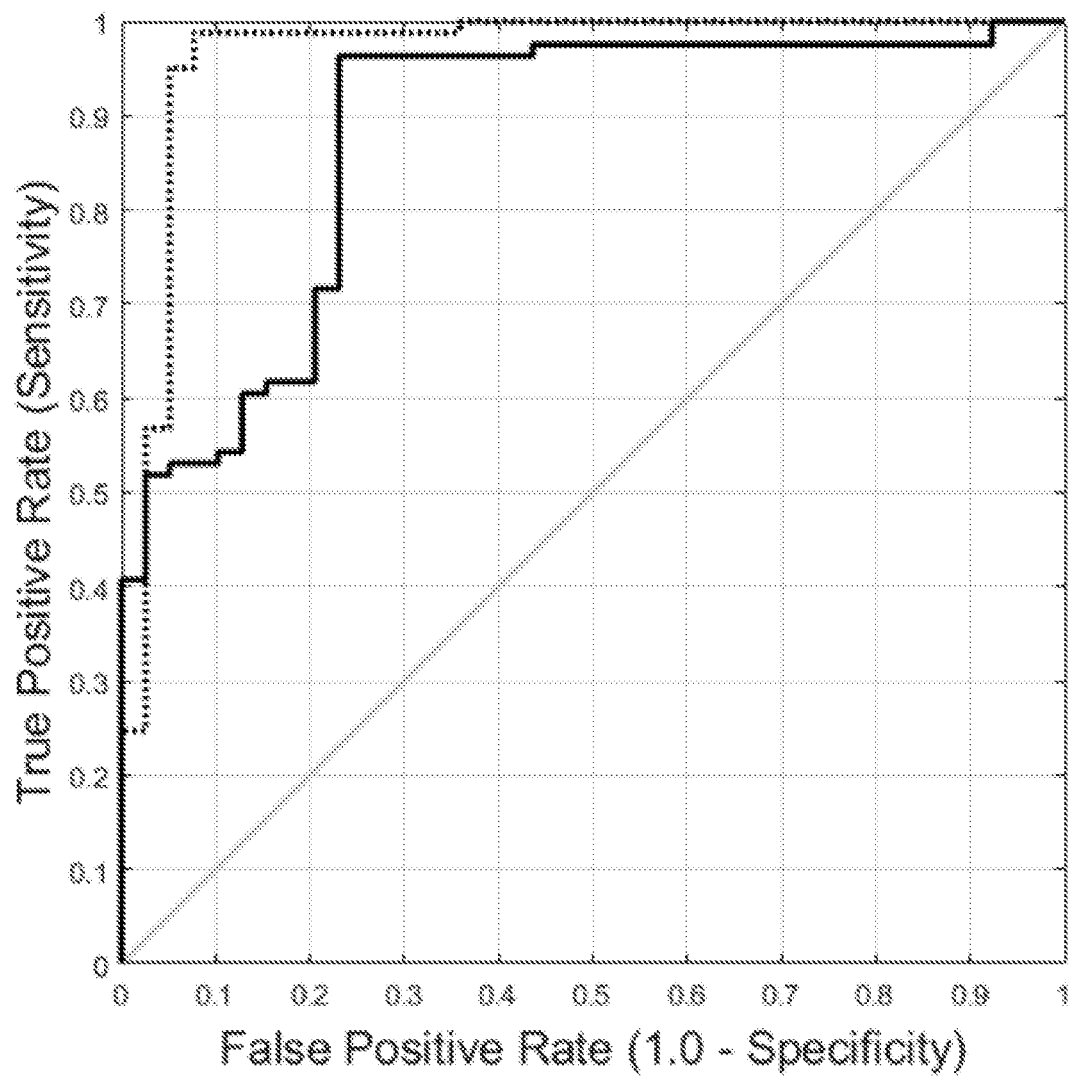

As another example shown in FIG. 18, a cascaded neural network is trained for screening malignant glioma by learning from the training data. The differential impedances and some of their derivatives from 10 kHz to 100 kHz are the input data for the cascaded artificial neural network. The dot line in FIG. 19 is the ROC for the training results of the cascaded neural network which is configured of 28 input neurons, 60 hidden neurons, and one output neuron. Although it shows that the very high sensitivity and specificity can be achieved using the neural network to classify the malignant gliomas during the training, its generality of the network performance should be validated by using unknown data. One validation method is called the leave-one-out method. The solid line is the ROC curve for the cross validation using the leave-one-out method for a cascaded network. These results indicate that a total accuracy of 90% (a sensitivity of 96% with a specificity of 77%) is achieved for this set of data.

When the lengths of transmission lines 112 and 131 are long enough, the system can be arranged to maximize the measurement sensitivity of screening malignant glioma, other brain tumors, and brain injuries, as described below.

When the length of transmission lines 112 or 131 is long enough, the measurements of the differential impedances of brain tissue will be changed. The brain tissue includes many different tissues such as the crani, cerebral spinal fluid (CSF), grey matter and white matter, and blood and blood vessels, etc. These different tissues have different values of conductivity and permittivity. For example, cerebral spinal fluid (CSF) has the highest conductivity among them, the grey and white matter have very high permittivity in low frequencies, and the conductivity of glioma is about 30% higher than its surrounding tissue, etc.

Figure 20:
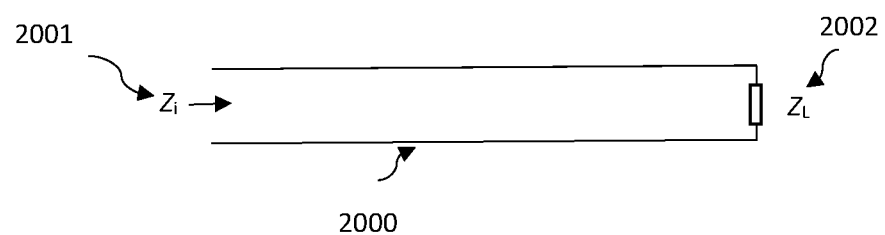

As abnormal tissue inside a head expands its volume, the volume of CSF decreases and the impedance distribution of brain tissue is changed, which is detected by the differential impedances. This detection sensitivity can be enhanced by carefully selecting the lengths of transmission lines 112 and 131. As shown in FIG. 20, when the length of the transmission line 2001 is long enough compared to the wavelength, the reflection needs to be considered. In general, the reflection needs to be considered when the length of the transmission line is higher than 1% of a wavelength. When the reflection exists, the normalized input impedance $z_{in}$ at the end of the excitation source becomes:

$$z_{in} = \frac{z_{in}}{z_0} = Z_0 \frac{z_L + j\tan(KL)}{1 + jz_L \tan(KL)} \quad (14)$$

where normalized load impedance $$z_L = \frac{1 + \Gamma}{1 - \Gamma},$$

wave number $K=2\pi/\lambda$, $\lambda$ is the wavelength, and $$\Gamma = \frac{z_L - z_0}{z_L + z_0}$$

is the reflection coefficient at the load, and $Z_0$ is the characteristic impedance of the transmission lines 1121 and 131 of FIG. 1, which is transmission line 2000 in FIG. 20.

Figure 21:
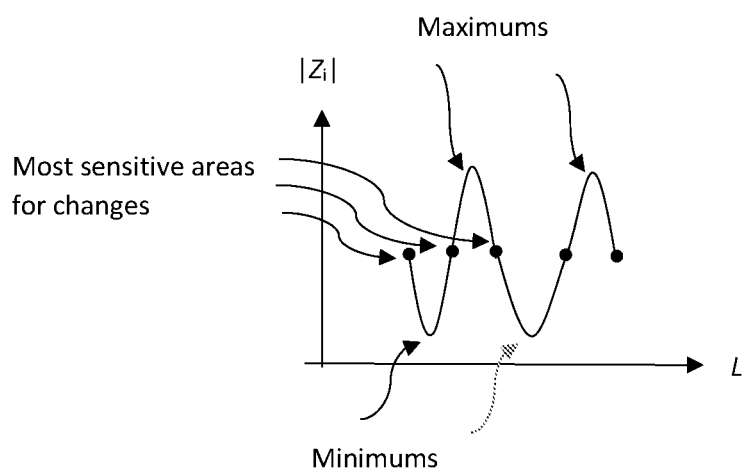

As the length L of the transmission line changes, the input impedance 2001 varies from capacitive to inductive according to equation (14) in a wide range, regardless the value of the load impedance 2002 which is the differential impedance for screening malignant glioma and brain injuries. As an example, the magnitude of the input impedance changing with the length of the transmission line is shown in FIG. 21, according to (14). As the length changes, the magnitude goes up and down. The magnitude of the input impedance changes rapidly in the middle area between the maximum and the minimum. The most sensitive areas are indicated in FIG. 21, where any disturbance of load impedance $Z_L$ induces a large change of input impedance $Z_L$ around the black dots in FIG. 21.

If the lengths of the transmission line 111 and 131 in FIG. 1 are selected so that the input impedance at the measurement side is matched to the average of the differential impedances of people without brain diseases and injuries, any change of brain tissue condition will induce large changes that affect the effective transmission due to the reflection, and will also induce a large change in the receiving differential impedance. As brain tissue changes due to malignant glioma or other injuries, the transmitted power and receiving signal rapidly change, which introduces a rapid change of differential impedances. This arrangement amplifies the changes of the tissue condition and maximizes the sensitivity of screening malignant glioma and other brain injuries.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A system for screening malignant glioma, other brain tumors, and brain injury in noninvasive way, the system comprising:
   a signal generator adapted to output electrical excitation signals; a transmitter circuit adapted to amplify, filter, and transmit the excitation signals to a brain tissue region;
   at least two transmission electrodes or coils adapted to be attached to a head of a subject at prescribed locations;
   a first transmission line with prescribed length to transmit the excitation signals from the transmitter to the transmission electrodes or coils;
   the at least two transmission electrodes or coils being adapted to emit the excitation signals to brain tissue;
   at least two receiving electrodes adapted to be located at two sides of the brain tissue at prescribed locations to detect the excitation signals that propagates through said-the brain tissue; at least one differential amplifier;
   a second transmission line with a prescribed length to transmit the detected excitation signals from the receiving electrodes to the at least one differential amplifier;
   the at least one differential amplifier being adapted to measure a difference of the excitation signals received from the receiving electrodes and generate an output corresponding to the difference;
   a receiver circuit adapted to amplify and filter the output of the differential amplifier and output the-an amplified and filtered output of the differential amplifier;
   an analog-to-digital convertors (ADCs) adapted to convert the output of the receiver circuit;
   a current sensor adapted to measure a current transmitted to the brain tissue;
   at least a switch array for multichannel switch to selectively connect the excitation signals and the at least one differential amplifiers to any of the at least two transmission electrodes or coils;
   a field-programmable-gate-array (FPGA) to select a form of the excitation signal, to provide digital excitation data to a digital-to-analog convertor (DAC) or a direct digital synthesis (DDS) for generating the excitation signal, to provide digital excitation data for controlling the signal generator, to acquire digitized data from the analog-to-digital convertors, and to provide timing signals and other control signals for the system operation;
   a computer to generate and transfer control data to the FPGA, receive data from the ADCs, conduct Fourier transform and spectral analysis, calculate parameters of frequency dispersion and harmonics, calculate differential impedances, calculate derivatives and statistics of the differential impedances, calculate nonlinearity of the brain tissue, and estimate a disturbance coefficient for the screening malignant gliomas, other brain tumors, and brain injuries.

2. The screening system as described in claim 1 wherein the disturbance coefficient is a sum of weighted parameters including receiving differential impedances and transmission differential impedances in a prescribed frequency range with different configurations and different excitation signals, frequency dispersions of the differential impedances, harmonics at prescribed frequencies, nonlinearity of the brain tissue, measurement distances, measurement configurations, and sex and age of a patient.

3. The screening system as described in claim 1 wherein the differential impedances include a receiving differential impedance and a transmission differential impedance obtained by detecting electrical fields induced by a prescribed excitation signal that is applied to electrodes or coils adapted to be disposed at two sides of the head of the subject with a prescribed frequency range and prescribed configuration.

4. The screening system as described in claim 1 wherein said excitation signals include sinusoidal signals, tone bursts, pulses, coded pulses, and chirps in a prescribed frequency range to measure the differential impedances, frequency responses, frequency dispersion, harmonic responses, nonlinearity, and disturbance coefficient of the brain tissue to indicate a likelihood of the malignant gliomas and brain injuries.

5. The screening system as described in claim 4 wherein the pulses is a single pulse, or a pulse sequence that has a prescribed pulse width and pulse repetition frequency for obtaining frequency response from the prescribed frequency range.

6. The screening system as described in claim 4 wherein said sinusoidal signal, tone bursts, and chirps have prescribed frequencies, pulse width, and pulse repetition frequency for obtaining frequency response from the prescribed frequency range.

7. The screening system as described in claim 4 wherein said coded pulses and chirps are received and detected by using digital orthogonal detectors in the computer to obtain the differential impedances with minimized effects of multipath, reflections, interference and noise to increase diagnosing sensitivity of the malignant glioma.

8. The screening system as described in claim 1 wherein the signal generator include a current source operating at a frequency that meets safety standards in a prescribed frequency range by automatically and adaptively controlling an amount of the current emitting from the current source according to the operating frequency.

9. The screening system as described in claim 1, wherein said the signal generator includes a band pass filter having a bandwidth that is automatically changed according to an operation frequency of the electrical excitation signals.

10. The screening system as described in claim 1 wherein each of said first and second transmission lines having a prescribed length has an input impedance and is selected for a particular frequency of the excitation signals so that the input impedance of the respective transmission line is at a middle point between maximum input impedance and minimum impedance to maximize detection sensitivity of the brain tissue variation due to malignant glioma, other brain tumors, and brain injuries.

11. The screening system as described in claim 1 wherein said diagnosing is noninvasive by applying said at least two transmission electrodes or coils to skin surface of the head of the subject for transmission and receiving said excitation signals.

12. The screening system as described in claim 1 wherein said at least two transmission electrodes or coils are adapted to be attached to skin surface of the head of the subject along squamosal sutures above ears for effective transmission and receiving the excitation signals.

13. The screening system as described in claim 1 wherein said at least two transmission electrodes or coils and receiving electrodes are selectively connected to transmitters and receivers, respectively, via the switch array.

14. The screening system as described in claim 1 wherein said transmitter and receivers are selectively connected to the at least two transmission electrodes and coils and the at least two receiving electrodes via the switch array so that the receiving impedance is calculated.

15. The screening system as described in claim 1 wherein said transmitter and receivers are selectively connected to two of the at least two transmission electrodes and coils and the at least two receiving electrodes via the switch array so that the transmission impedance is calculated.

16. The screening system as described in claim 1 wherein said differential impedance is a difference of impedances at two receiving locations on the head of the subject.

17. The screening system as described in claim 1 wherein the differential impedances are analyzed for a magnitude, phase, and frequency dispersion to describe the difference of brain tissues between normal people and patients having the malignant glioma or other brain tumors or brain injuries.

18. The screening system as described in claim 1 wherein said nonlinearity of the brain tissue is obtained by analyzing high harmonics of the brain tissue responses to a sinusoidal excitation signal that has a single frequency for screening the malignant glioma, other brain tumors, and brain injury.

19. The screening system as described in claim 1 wherein said disturbance coefficient is a weighted sum of the differential impedances and their derivatives, normalized harmonic difference, nonlinearity of the brain tissue frequency response, and is calculated according to $$D = \sum_{i=1}^{M} a_i Z_r(\omega_i) + \sum_{i=1}^{M} b_i Z_t(\omega_i) + \sum_{i=1}^{M} c_i \Phi_r(\omega_i) +$$
$$\sum_{i=1}^{M} d_i \Phi_t(\omega_i) + \sum_{i}^{M} e_i \frac{dZ_r(\omega_i)}{d\omega} + \sum_{i}^{M} f_i \frac{d\Phi_r(\omega_i)}{d\omega} + \sum_{i=1}^{M} g_i \frac{Z_r(\omega_i)}{Z_t(\omega_i)} +$$
$$\sum_{i=1}^{N} h_i \Delta M_i + \sum_{i=1}^{N} o_i \Delta \theta_i + \sum_{i=1}^{L} p_i \Delta M_{ni} + \sum_{i=1}^{L} q_i \Delta \theta_{ni}$$

where M is a number of frequencies selected for analysis, N is a number of harmonics for frequency dispersion analysis, L is a number of high harmonics for nonlinearity analysis, weighting constants $a_i$, $b_i$, $c_i$, $d_i$, $e_i$, $f_i$, $g_i$, $h_i$, $o_i$, $p_i$, $q_i$, $w_i$, $v_i$ are estimated by data analysis or artificial neural network for screening malignant glioma, other brain tumors, and brain injuries, $Z_r(\omega_i)$ and $\Phi_r(\omega_i)$ are magnitude and phase of receiving differential impedance at frequency $\omega_i$, $Z_t(\omega_i)$ and $\Phi_t(\omega_i)$ are magnitude and phase of transmission differential impedance at frequency $\omega_i$, $\Delta M_i$ and $\Delta \theta_i$ are normalized magnitude difference and phase difference at frequency $\omega_i$, $\Delta M_{ni}$ and $\Delta \theta_{ni}$ are normalized magnitude difference and phase difference at high harmonic $\omega_i$ for nonlinearity measurements, other factors includes medical diagnostic information (such as blood tests and medical imaging information, and other pathological information), head circumference, direct distance from one side of a head to another side, skin condition, age, sex, etc.

20. The screening system as described in claim 1 wherein said disturbance coefficient is a function of the differential impedances and their derivatives, normalized harmonic difference, nonlinearity of the brain tissue frequency response, and is calculated according to $$D = f\Big(Z_r(\omega_i), Z_t(\omega_i), \Phi_r(\omega_i), \Phi_t(\omega_i),$$
$$\frac{dZ_r(\omega_i)}{d\omega}, \frac{d\Phi_r(\omega_i)}{d\omega}, \frac{Z_r(\omega_i)}{Z_t(\omega_i)}, \Delta M_j, \Delta \theta_j, \Delta M_{nk} \Delta \theta_{nk}\Big)$$

where i=1, 2, 3 . . . , M; j=1, 2, 3 . . . , N; k=1, 2, 3 . . . L, and the function is a nonlinear function that maps measurements and input parameters to the disturbance coefficient to increase the sensitivity and specificity of the screening.

21. The screening system as described in claim 1 wherein said disturbance coefficient is estimated by using an artificial neural network and clinical data collected by the screening system and pathological information of patients.

22. The screen system as described in claim 21 wherein said artificial neural network is trained by using all input data for calculating the disturbance coefficient.

23. The screening system of claim 21 wherein said artificial neural network provides a likelihood of the malignant glioma, other brain tumor, brain injuries, and normal.

24. The screening system as described in claim 19 wherein said disturbance coefficient is analyzed by using the Receiver Operating Characteristic (ROC) curve as guidance to screen the malignant glioma, other brain tumors, and brain injury with a likelihood value based on sensitivity and specificity.

* * * * *